United States Patent
Eggen et al.

(10) Patent No.: US 8,948,883 B2
(45) Date of Patent: Feb. 3, 2015

(54) ELECTRODE ASSEMBLIES AND ASSOCIATED FIXATION MEMBERS FOR IMPLANTABLE MEDICAL DEVICES

(71) Applicant: Medtronic, Inc., Minneapolis, MN (US)

(72) Inventors: Michael D Eggen, Lake Elmo, MN (US); Zhongping Yang, Woodbury, MN (US); Rick D McVenes, Isanti, MN (US); Noelle C Hurtig, Minneapolis, MN (US); Raymond W Usher, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/869,509

(22) Filed: Apr. 24, 2013

(65) Prior Publication Data

US 2014/0324145 A1    Oct. 30, 2014

(51) Int. Cl.
*A61N 1/05*    (2006.01)

(52) U.S. Cl.
CPC ..................... *A61N 1/059* (2013.01)
USPC .......................... 607/127; 607/119

(58) Field of Classification Search
None
See application file for complete search history.

(56) References Cited

U.S. PATENT DOCUMENTS

| | | | |
|---|---|---|---|
| 5,443,492 | A | 8/1995 | Stokes et al. |
| 7,212,870 | B1 | 5/2007 | Helland |
| 8,010,209 | B2 | 8/2011 | Jacobson |
| 2009/0204170 | A1 | 8/2009 | Hastings et al. |
| 2010/0114280 | A1 | 5/2010 | Hill et al. |
| 2010/0198288 | A1 | 8/2010 | Ostroff |
| 2011/0307043 | A1 | 12/2011 | Ollivier |

FOREIGN PATENT DOCUMENTS

| | | |
|---|---|---|
| WO | WO 2007/073435 A1 | 6/2007 |
| WO | WO 2009/006531 A1 | 1/2009 |

OTHER PUBLICATIONS (PCT/US2014/034155) PCT Notification of Transmittal of the International Search Report and the Written Opinion of the International Searching Authority.

*Primary Examiner* — Michael Kahelin
(74) *Attorney, Agent, or Firm* — Evans M. Mburu

(57) ABSTRACT

A fixation member of an electrode assembly for an implantable medical device includes a tissue engaging portion extending along a circular path, between a piercing distal tip thereof and a fixed end of the member. The circular path extends around a longitudinal axis of the assembly. A helical structure of the assembly, which includes an electrode surface formed thereon and a piercing distal tip, also extends around the longitudinal axis and is located within a perimeter of the circular path. The tissue engaging portion of the fixation member extends from the distal tip thereof in a direction along the circular path that is the same as that in which the helical structure extends from the distal tip thereof. The electrode assembly may include a pair of the fixation members, wherein each tissue engaging portion may extend approximately one half turn along the circular path.

11 Claims, 5 Drawing Sheets

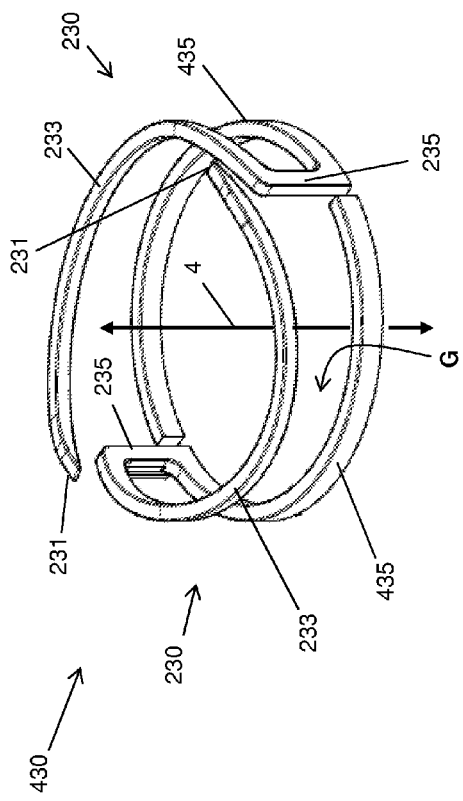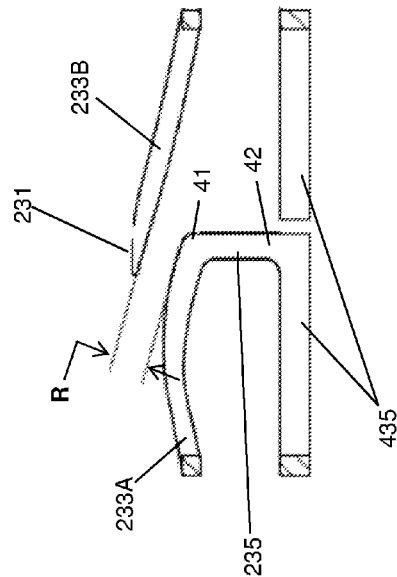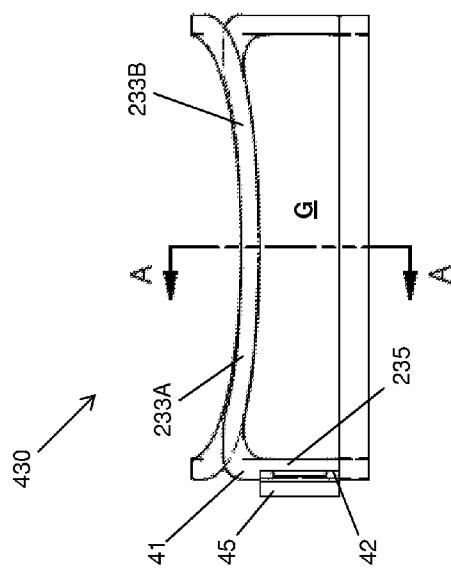

US 8,948,883 B2

ELECTRODE ASSEMBLIES AND ASSOCIATED FIXATION MEMBERS FOR IMPLANTABLE MEDICAL DEVICES

TECHNICAL FIELD

The present invention pertains to implantable medical devices, and, more specifically, to electrode assemblies thereof.

BACKGROUND

Many electrode assemblies of implantable medical devices, for the delivery of stimulation therapy and/or for diagnostic sensing, include fixation members configured to hold an electrode surface of the assembly in stable and intimate contact with tissue at an implant site. Those skilled in the art are familiar with electrode assemblies that include a helical structure; the helical structure typically includes a piercing distal tip to engage with tissue so that the helical structure may be screwed into the tissue and thereby fix an electrode surface of the assembly in intimate contact with the tissue. In some of these electrode assemblies the electrode surface is formed directly on the helical structure. Although such a helical structure can provide adequate fixation in many types of electrode assemblies, there is a need for new types of electrode assemblies and associated fixation members.

SUMMARY

Embodiments of the present invention encompass implantable medical devices (e.g., cardiac pacemakers), electrode assemblies thereof, and fixation members for the electrode assemblies. According to some embodiments, a fixation member for an electrode assembly, includes a tissue engaging portion that extends along a circular path, between a piercing distal tip thereof and a coupling portion, or a fixed end, of the member, which is configured to be fixedly attached to a distal portion of the device. The circular path extends around a longitudinal axis of the fixation member and of the electrode assembly, and the electrode assembly further includes a helical structure that has an electrode surface formed thereon, and a piercing distal tip adjacent thereto; the helical structure is located within a perimeter of the circular path and also extends around the longitudinal axis. The tissue engaging portion of the fixation member extends from the distal tip thereof in a direction along the circular path that is the same as that in which the helical structure extends from the distal tip thereof. Thus, rotation of the distal portion of the device, when the piercing distal tips of the helical structure and the fixation member are positioned in proximity to a target implant site, causes both the helical structure and the tissue engaging portion of the fixation member to engage within tissue at the implant site.

An implantable medical device, according to some embodiments, comprises a relatively compact, or miniature capsule in which a pulse generator and power source are hermetically sealed, and to which the electrode assembly is directly coupled. In some embodiments, an outer diameter of the helical structure is approximately 2 French, while an outer diameter defined by the tissue engaging portion of the fixation member is approximately 20 French; and the electrode surface formed on the helical structure is preferably formed for 'high impedance' pacing, for example, having a gross surface area of approximately 1 to 2 square millimeters and an increased microscopic surface area, for example, being formed as a titanium nitride (TiN) coating overlaying the helical structure. According to some embodiments, another electrode surface is formed on the fixation member, for example, to form a bipolar pace-sense pair with the electrode surface formed on the helical structure.

Electrode assemblies, according to some preferred embodiments, include a pair of the above-described fixation members, for example, wherein the fixed ends thereof are located opposite one another, on either side of the helical structure. The tissue engaging portion of each fixation member may extend between approximately one quarter of a turn and approximately one turn along the circular path, preferably, approximately one half of a turn. The piercing distal tip of each fixation member may be coplanar with that of the helical structure, or proximally offset therefrom.

In some embodiments, the coupling portion, or fixed end, of the fixation member includes a post that is offset from, and extends approximately parallel with the longitudinal axis, and the tissue engaging portion of the fixation member includes a first segment and a second segment, wherein the first segment extends along the circular path and proximally from the post, in a longitudinal direction, and the second segment extends along the circular path and distally from the first segment to the distal tip, in an opposite longitudinal direction. Thus, the tissue engaging portion, according to these embodiments of the fixation member has a contour that may be likened to a saddle shape, wherein a gap between the distal portion of the device and the tissue engaging portion of the fixation member narrows in between the piercing distal tip thereof and the post of the coupling portion to create a kind of lock on the tissue with which the fixation member is engaged.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 4A is a perspective view of a pair of fixation members, according to some embodiments;

FIG. 4B is an elevation view of the pair of fixation members; and

FIG. 4C is a cross-section view through section line A-A of FIG. 4B.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
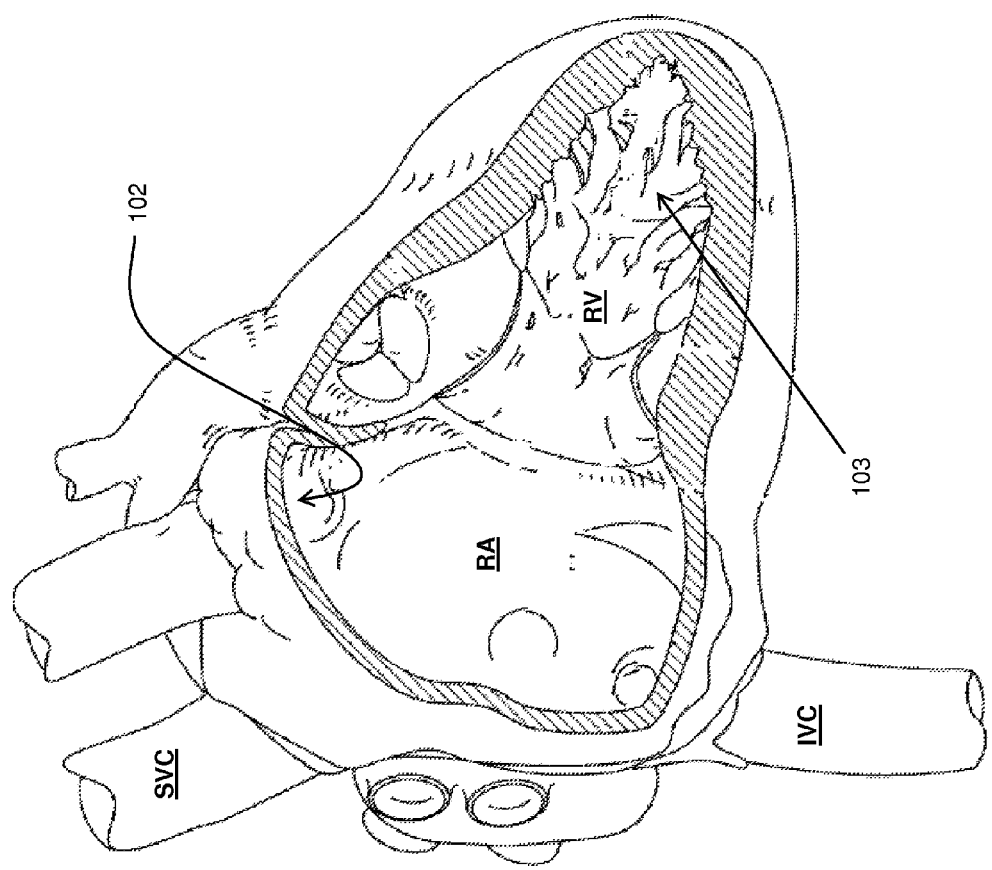
FIG. 1 is a schematic diagram showing potential implant sites for embodiments of the present invention.
Figure 2A:
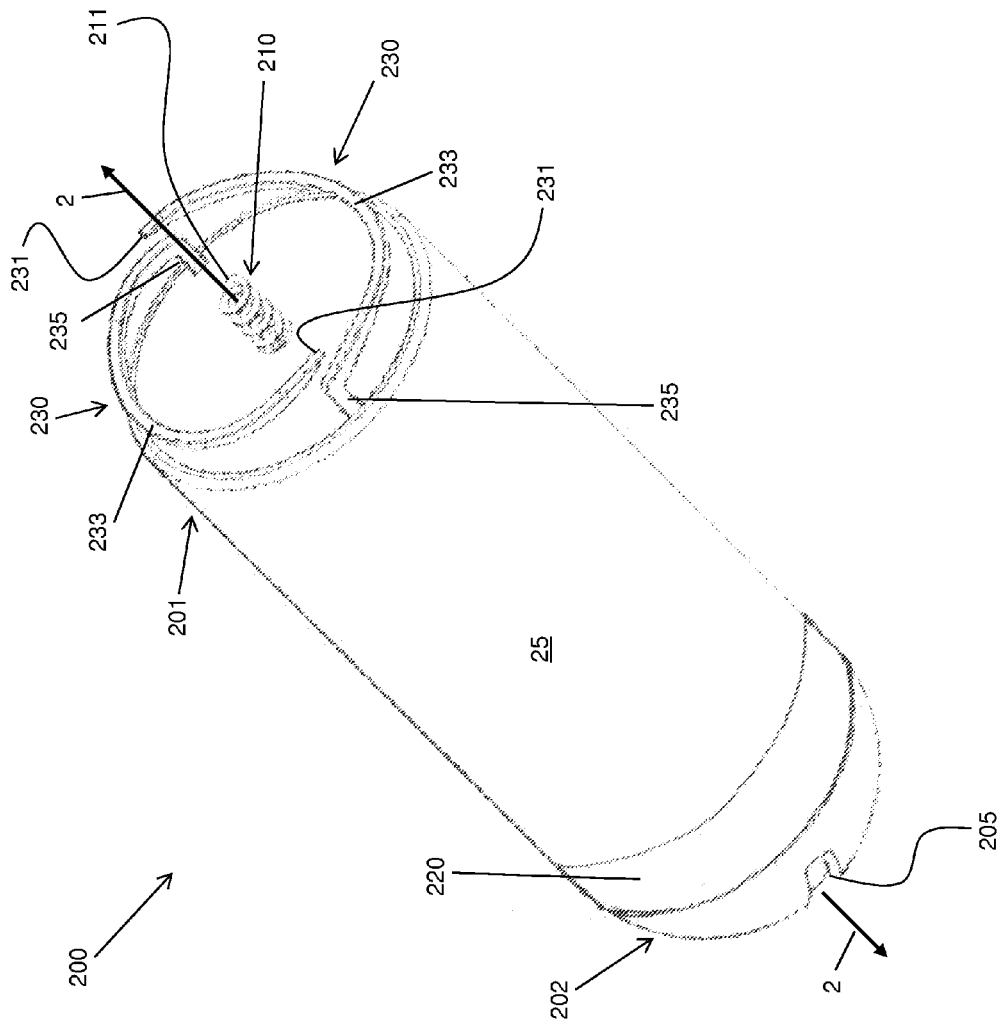
FIG. 2A is a perspective view of an implantable medical device, according to some embodiments.

FIG. 1 is a schematic diagram showing the interior of a right atrium RA and a right ventricle RV of a heart. FIG. 1 illustrates some potential endocardial implant sites 102, 103 for implantable electrode assemblies, according to embodiments of the present invention, for example, like that shown in FIG. 2A. It should be noted that any other suitable implant site, either endocardial or epicardial, may be selected for electrode assembly embodiments. FIG. 2A is a perspective view of an implantable medical device 200, wherein the electrode assembly thereof includes a helical structure 210, which extends distally from a distal portion 201 of device 200, and around a longitudinal axis 2 of the electrode assembly, and on which a first electrode surface is formed, and a ring structure 220, on which a second electrode surface is formed. The pair of electrode surfaces can provide bipolar pacing and sensing at either of implant sites 102, 103 shown in FIG. 1. According to the illustrated embodiment, both pulse generator electronic circuitry and a battery power source of device 200 are contained within a relatively compact, or miniature, hermetically sealed capsule 25 thereof, for example, that has a length of approximately 2 to 2.5 centimeters and a diameter of approximately 20 French (6-7 millimeters). Capsule 25 is preferably formed from a biocompatible and biostable metal such as titanium, which is overlaid with an insulative layer, for example, parylene, polyimide, medical grade polyurethane, Polyether ether ketone (PEEK), or silicone. Hermetic feedthroughs, such as any known to those skilled in the art, couple each electrode surface to the pulse generator circuitry contained within capsule 25, which is configured, according to methods known to those skilled in art, to sense, via the electrode surfaces, either atrial depolarization (i.e. P-waves), for example, from implant site 102, or ventricular depolarization (i.e. R-waves), for example, from implant site 103, and to apply stimulation pulses to the myocardial tissue for cardiac pacing when necessary.

With further reference to FIG. 2A, helical structure 210 is preferably configured for high impedance pacing from the electrode surface thereof; thus, according to an exemplary embodiment, helical structure 210 has an outer diameter of approximately 2 French (0.6-0.7 millimeters), and the gross surface area of the electrode surface is between approximately 1 square millimeter and approximately 2 square millimeters. In some embodiments, the electrode surface is formed along an outer portion of helical structure 210, while an inner portion thereof is insulated. Those skilled in the art will appreciate that the high impedance of this electrode surface, resultant of the relatively small gross surface area thereof, provides relatively efficient pacing stimulation, for example, to maximize the life of the battery power source of device 200. Helical structure 210 may be formed from a platinum iridium wire or a tantalum wire, for example, having an outer diameter of between approximately 0.005 inch (0.13 mm) and approximately 0.010 inch (0.25 mm); and the electrode surface of helical structure 210 may be formed by a titanium nitride (TiN) coating that increases the microscopic surface area of the electrode surface for an enhanced interface with the myocardial tissue, for example, at either of implant sites 102, 103. Ring structure 220 may likewise be formed of either platinum iridium or tantalum and have a TiN coating that forms the second electrode surface, which may have a surface area of approximately 50 millimeters, according to some embodiments.

Intimate contact between the electrode surface of helical structure 210 and the myocardial tissue is attained by engaging a piercing distal tip 211 of helical structure 210 in the tissue and then rotating structure 210 counter-clockwise, according to FIG. 2A, to screw structure 210 into the tissue. In order to stabilize and maintain this intimate tissue contact of the electrode surface of helical structure 210, the electrode assembly of device 200 further includes one or a pair of fixation members 230.

FIG. 2A illustrates each fixation member 230 including a tissue engaging portion 233, which is terminated by a piercing distal tip 231, wherein each tissue engaging portion 233 extends from the distal tip 231 thereof, along a circular path, which defines a perimeter in which helical structure 210 is located. With further reference to FIG. 2A, tissue engaging portion 233 of each fixation member 230 extends along the circular path toward a fixed end, which is coupled to distal portion 201 of device 200, and which includes a post 235 extending distally from distal portion 201. Posts 235 are shown located opposite one another on either side of helix structure 210, being radially offset from, and extending approximately parallel with, longitudinal axis 2. According to the illustrated embodiment, the direction along the circular path, in which each tissue engaging portion 233 extends from the corresponding distal tip 231, is the same as in which helical structure 210 extends from piercing distal tip 211 thereof, which is clockwise according to FIG. 2A. Thus, according to those embodiments in which helical structure 210 is fixedly attached to distal portion 201 of device 200, like fixation members 230, and when piercing distal tips 211 and 231 are positioned in proximity to a target implant site (e.g., site 102 or 103) for engagement with myocardial tissue, device 200 as a whole may be rotated, for example, in the counter-clockwise direction, according to FIG. 2A (i.e. per arrow F of FIGS. 2B and 3), to screw both helical structure 210 and fixation members 230 into the tissue. Although FIG. 2A illustrates each tissue engaging portion 233 extending approximately one half of a turn along the circular path, in alternate embodiments each portion 233 may extend between approximately one quarter of a turn to approximately one full turn around the circular path.

Figure 2B:
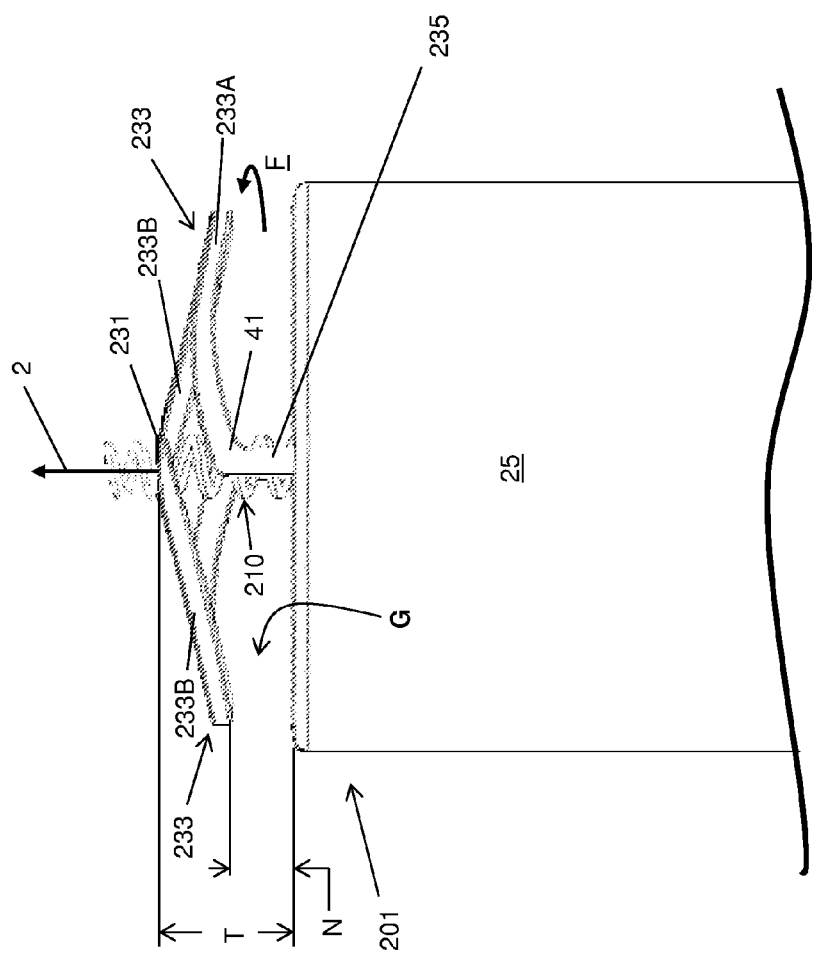
FIG. 2B is an elevation view of a portion of an electrode assembly of the device, according to some embodiments.

FIG. 2B is an elevation view of a portion of the electrode assembly of device 200 wherein a contour of each tissue engaging portion 233, according to some embodiments, as it extends along the circular path is more clearly seen. FIG. 2B illustrates each tissue engaging portion 233 including a first segment 233A, which extends along the circular path and bends proximally from a distal end 41 of the corresponding post 235, toward distal portion 201 of device 200, and a second segment 233B, which extends along the circular path and distally from the corresponding first segment 233A, away from distal portion 201. According to the illustrated embodiment, piercing distal tips 231 of fixation members 230 and piercing distal tip 211 of helical structure 210 (FIG. 2A) are coplanar with one another and spaced at a distance T from distal portion 201, wherein distance T may be between approximately 1 millimeter and approximately 3 millimeters. According to some preferred embodiments, a pitch of helical structure 210 (e.g., approximately 0.016 inch) is less than or equal to that defined by tissue engaging portion 233 between distal end 41 of post 235 and piercing distal tip 231. According to some alternate embodiments, as illustrated by the broken lines in FIG. 2B, helical structure 210 may extend beyond distal tips 231, so that distal tips 231 are proximally offset from distal tip 211 of helical structure 210, in which case helical structure 210 may engage within tissue at the target implant site ahead of the engagement of one or both of portions 233, depending on the character, or structure of the surface of the tissue at the site, and an orientation of the electrode assembly relative to the surface. With further reference to FIG. 2B, in conjunction with FIGS. 4A-C, the above described contour of each tissue engaging portion 233 may be likened to a saddle shape, wherein a gap G between distal portion 201 and tissue engaging portion 233 narrows to a distance N, in between piercing distal tip 231 and post 235, to create a kind of lock on the tissue with which portion 233 is engaged.

Figure 3:
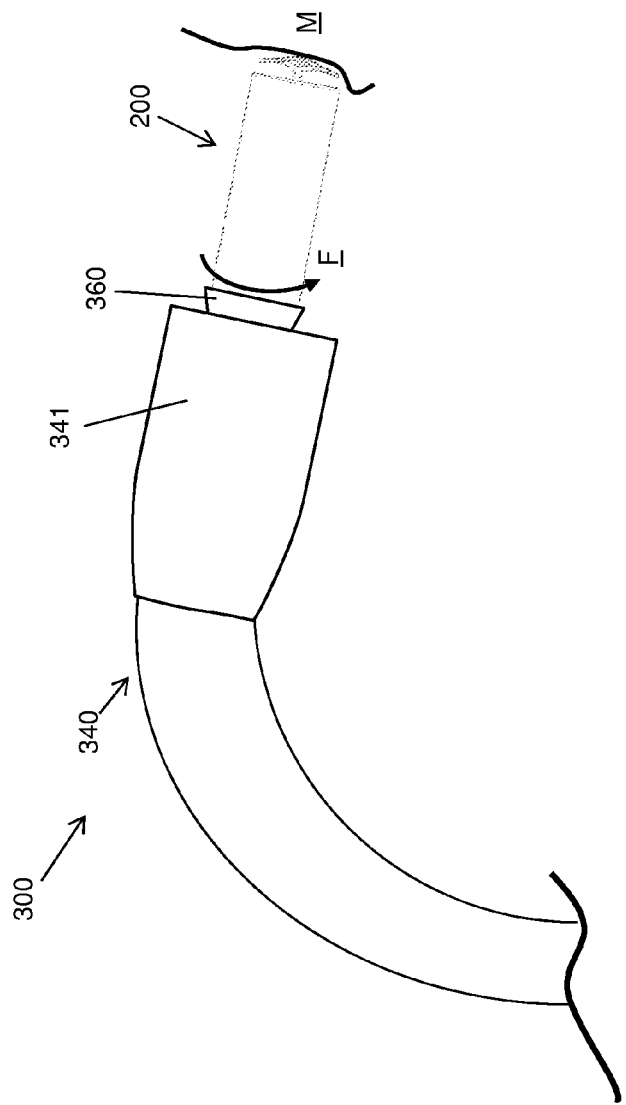
FIG. 3 is a plan view of a distal portion of a delivery device engaging the medical device, according to some methods.

As was mentioned above, in those embodiments wherein both helical structure 210 and one or a pair of fixation members 230 are fixedly attached to distal portion 201 of device 200, device 200 may be rotated to engage helical structure 210 and fixation member(s) 230 in tissue at a target implant site. With reference to FIG. 3, and according to some implant methods, a delivery device 300 may be configured with an outer sheath 340 and a telescoping inner member 360 that is configured to engage around a proximal portion 202 (FIG. 2A) of device 200. With reference back to FIG. 1, delivery device 300, with device 200 loaded into a distal portion 341 of outer sheath 340, may be inserted into the vascular system of a patient, for example, via a percutaneous entry site, and distal portion 341 passed into the heart, via an inferior vena cava IVC or a superior vena cava SVC thereof. Once distal portion 341 is located in proximity to a target implant site, for example, one of sites 102, 103, inner member 360 may be advanced, relative to outer sheath 340, to push device 200 out from a distal opening of distal portion 341 and into contact with the site, and then inner member 360 may be rotated, per arrow F, to fix device in tissue M at the target implant site. With reference back to FIG. 2A, according to some embodiments, device 200 includes a notch 205, which is formed in proximal portion 202 and configured for engagement with a screw-driver type stylet, wherein the tool may replace or form a part of telescoping inner member 360 that rotates device 200 per arrow F.

It should be noted that, according to some embodiments, an electrode surface may be formed on one or both of fixation members 230 to function as a bipolar pace-sense pair with the above-described electrode surface formed on helical structure 210. Such a pace-sense pair may be advantageous in some instances, over the pace-sense pair formed with the electrode surface of ring structure 220, for example, when device 200 is implanted in the right atrium RA for pacing function based on P-wave sensing, since the closer spacing between the electrode surface of helical structure 210 and that of one or both of fixation members 230 is less susceptible to far-field R-wave sensing.

FIG. 4A is a perspective view of a pair 430 of fixation members 230, wherein pair 430 may be machined, or cut, from a tubular member, according to some embodiments. FIG. 4B is an elevation view of pair 430; and FIG. 4C is a cross-section view through section line A-A of FIG. 4B. FIGS. 4A-C illustrate a coupling portion of each fixation member 230 including the aforementioned post 235 and a base segment 435, which extends from a proximal end 42 of post 235 and along a circular path, which is offset from the above-described circular path along which tissue engaging portions 233 extend. With reference back to FIGS. 2A-B, base segments 435 may be fixed and embedded within distal portion 201 of device 200, and thus hidden from view in these Figures. It should be noted that, in alternate embodiments, base segments 435 may extend in different paths, either arcuate or relatively straight. But, according to the illustrated embodiment, because pair 430 of fixation members 230 is cut from a tubular member, both circular paths (of tissue securing portions 233 and base segments 435) extend around a longitudinal axis 4 of the tubular member. The tubular member from which pair 430 is cut may be any suitable biocompatible and rigid material, preferably a metallic material, for example, titanium or tantalum.

According to the illustrated embodiment, and with reference to FIG. 4B, in conjunction with FIG. 2B, it may be seen that a central cross-section, per section line A-A (aligned on axis 4), divides first segment 233A of each tissue engaging portion 233 from the corresponding second segment 233B and, thus, coincides with the above-described narrowing of gap G. FIGS. 4A-B further illustrates one of posts 235 including an optional extension 45 that protrudes radially outward, away from longitudinal axis 4. Extension 45 may serve as a tissue stop, when tissue engaging portions 233 are being screwed into tissue, for example, as described above.

FIG. 4C illustrates a rectangular cross-section of each base segment 435 and of each tissue engaging portion 233, wherein, according to an exemplary embodiment, the cross section of each tissue engaging portion 233 is approximately 0.005 inch by 0.010 inch, and may vary slightly in size to enhance a strength thereof. FIG. 4C further illustrates piercing distal tip 231 of one of tissue engaging portions 233 extending over first segment 233A of the other of portions 233, and spaced apart therefrom by a distance R. According to an exemplary embodiment distance R is approximately 0.018 inch.

In the foregoing detailed description, the invention has been described with reference to specific embodiments. However, it may be appreciated that various modifications and changes can be made without departing from the scope of the invention as set forth in the appended claims. For example, although exemplary embodiments of electrode assemblies have been described in the context of device 200, the described electrode assemblies may be incorporated by implantable medical electrical leads that are configured to couple with separate pulse generator devices and extend distally therefrom, for example, into chambers of a heart.

The invention claimed is:

1. An implantable medical device comprising a pulse generator, a power source, an hermetically sealed capsule that contains the pulse generator and the power source, and an electrode assembly, the electrode assembly comprising a longitudinal axis, a helical structure coupled to the capsule and extending distally from the capsule and around the longitudinal axis, a first electrode surface formed on the helical structure, and a second electrode surface electrically isolated from the first electrode surface, the helical structure including a piercing distal tip located adjacent the first electrode surface; and an improvement to the device comprising at least one fixation member, wherein each fixation member comprises:

a fixed end coupled to the capsule, the fixed end comprising a post that extends approximately parallel with the longitudinal axis, between the distal portion of the device and the tissue engaging portion of the corresponding fixation member; and a tissue engaging portion terminated by a piercing distal tip, each tissue engaging portion extending from the corresponding distal tip to the corresponding fixed end along a circular path, the helical structure being located within a perimeter of the circular path; and wherein each tissue engaging portion extends from the piercing distal tip thereof in a direction along the circular path that is the same as that in which the helical structure extends from the piercing distal tip thereof, either clockwise or counter-clockwise, and wherein the fixed end of each fixation member of the electrode assembly further comprises a base segment from which the corresponding post extends distally to the corresponding tissue engaging portion, the base segment of each fixation member extending along an arcuate path, around the longitudinal axis.

2. The device of claim 1, wherein the tissue engaging portion of each fixation member of the electrode assembly extends between approximately one quarter of a turn and approximately one turn along the circular path.

3. The device of claim 1, wherein the piercing distal tip of each fixation member of the electrode assembly is approximately coplanar with the piercing distal tip of the helical structure.

4. The device of claim 1, wherein the piercing distal tip of each fixation member of the electrode assembly is proximally offset from the piercing distal tip of the helical structure.

5. The device of claim 1, wherein the second electrode surface of the electrode assembly is formed on the fixation member of the electrode assembly.

6. The device of claim 1, wherein the electrode assembly further comprises a ring structure that extends around a perimeter of the capsule, and the second electrode surface is formed on the ring structure.

7. The device of claim 6, wherein the electrode assembly further comprises a third electrode surface formed on the fixation member thereof.

8. The device of claim 1, wherein an outer diameter of the helical structure of the electrode assembly is approximately 2 French, and an outer diameter defined by the tissue engaging portion of each fixation member of the electrode assembly is approximately 20 French.

9. The device of claim 1, wherein a gross surface area of the first electrode surface is between approximately 1 square millimeter and approximately 2 square millimeters.

10. The device of claim 1, wherein the first electrode surface comprises a TiN coating that overlays the helical structure.

11. An implantable medical device comprising a pulse generator, a power source, an hermetically sealed capsule that contains the pulse generator and the power source, and an electrode assembly, the electrode assembly comprising a longitudinal axis, a helical structure coupled to the capsule and extending distally from the capsule and around the longitudinal axis, a first electrode surface formed on the helical structure, and a second electrode surface electrically isolated from the first electrode surface, the helical structure including a piercing distal tip located adjacent the first electrode surface; and an improvement to the device comprising at least one fixation member, wherein each fixation member comprises:

a fixed end coupled to the capsule, the fixed end comprising a post that extends approximately parallel with the longitudinal axis, between the distal portion of the device and the tissue engaging portion of the corresponding fixation member; and a tissue engaging portion terminated by a piercing distal tip, each tissue engaging portion extending from the corresponding distal tip to the corresponding fixed end along a circular path, the helical structure being located within a perimeter of the circular path; and wherein each tissue engaging portion extends from the piercing distal tip thereof in a direction along the circular path that is the same as that in which the helical structure extends from the piercing distal tip thereof, either clockwise or counter-clockwise, and wherein the tissue engaging portion of each fixation member of the electrode assembly includes a first segment and a second segment, each first segment extending along the circular path and bending proximally from the corresponding post, toward the capsule of the device, and each second segment extending along the circular path and distally from the corresponding first segment, away from the capsule of the device.

* * * * *